(12) United States Patent
Renaud et al.

(10) Patent No.: US 8,845,691 B2
(45) Date of Patent: Sep. 30, 2014

(54) OSSEOUS ANCHORING IMPLANT WITH A POLYAXIAL HEAD AND METHOD FOR INSTALLING THE IMPLANT

(75) Inventors: Christian Renaud, Arthes (FR); Gerard Castera, Cabries (FR)

(73) Assignee: LDR Medical, Rosieres Pres Troyes (FR)

(*) Notice: Subject to any disclaimer, the term of this patent is extended or adjusted under 35 U.S.C. 154(b) by 2280 days.

(21) Appl. No.: 10/570,080

(22) PCT Filed: Sep. 1, 2004

(86) PCT No.: PCT/IB2004/002825
§ 371 (c)(1),
(2), (4) Date: Jun. 9, 2006

(87) PCT Pub. No.: WO2005/020829
PCT Pub. Date: Mar. 10, 2005

(65) Prior Publication Data
US 2006/0282074 A1    Dec. 14, 2006

(30) Foreign Application Priority Data
Sep. 1, 2003    (FR) ...................................... 03 10363

(51) Int. Cl.
*A61B 17/70*    (2006.01)

(52) U.S. Cl.
CPC .......... *A61B 17/7035* (2013.01); *A61B 17/7041* (2013.01)
USPC ........................................................ 606/264

(58) Field of Classification Search
USPC .................................. 606/300–331, 246–279
See application file for complete search history.

(56) References Cited

U.S. PATENT DOCUMENTS

| 4,041,939 A | 8/1977 | Hall |
| 4,047,524 A | 9/1977 | Hall |

(Continued)

FOREIGN PATENT DOCUMENTS

| CA | 1304267 | 6/1992 |
| CA | 2443215 | 10/2002 |

(Continued)

OTHER PUBLICATIONS

A unique self-contained connexion; Website: www.ldrmedical.dr/connexion_uk.htm; Oct. 11, 2004.

(Continued)

*Primary Examiner* — Andrew Yang
*Assistant Examiner* — Diana S Jones
(74) *Attorney, Agent, or Firm* — Denko Coburn Lauff LLP

(57) ABSTRACT

An osseous anchoring implant, various embodiments of which comprise an osseous anchor and a head bearing fixation structure capable of receiving and fixing at least one bar, the head of the implant being traversed by at least one duct, which receives the bar through a lateral aperture, and by a threaded channel, whose axis is not parallel to the axis of the duct, which receives a fixation screw of the bar, the implant being characterized in that it comprises fixation structure of the head on the part of the implant which extends from the osseous anchor, these fixation structures allowing, prior to blocking and fixing, at least a determined mobility of the head around at least one axis not parallel to the axis of symmetry of the osseous anchor. The fixation screw of the bar may comprise a ball and socket at its base.

2 Claims, 6 Drawing Sheets

(56) References Cited

U.S. PATENT DOCUMENTS

| | | | |
|---|---|---|---|
| 4,055,385 A | 10/1977 | Bjors | |
| 4,429,690 A | 2/1984 | Angelino-Pevani | |
| 4,648,388 A | 3/1987 | Steffee | |
| 4,653,481 A | 3/1987 | Howland et al. | |
| 4,696,290 A | 9/1987 | Steffee | |
| 4,773,402 A | 9/1988 | Asher et al. | |
| 4,946,458 A | 8/1990 | Harms et al. | |
| 5,024,213 A | 6/1991 | Asher et al. | |
| 5,067,955 A | 11/1991 | Cotrel | |
| 5,092,893 A | 3/1992 | Smith | |
| 5,129,899 A | 7/1992 | Small et al. | |
| 5,176,680 A | 1/1993 | Vignaud et al. | |
| 5,197,986 A | 3/1993 | Mikhail | |
| 5,226,766 A | 7/1993 | Lasner | |
| 5,269,784 A | 12/1993 | Mast | |
| 5,275,600 A | 1/1994 | Allard et al. | |
| 5,282,863 A | 2/1994 | Burton | |
| 5,314,477 A | 5/1994 | Marnay | |
| 5,330,473 A | 7/1994 | Howland | |
| 5,344,421 A | 9/1994 | Crook et al. | |
| 5,358,526 A | 10/1994 | Tornier | |
| 5,374,267 A | 12/1994 | Siegal | |
| 5,401,269 A | 3/1995 | Buttner-Janz et al. | |
| 5,437,669 A | 8/1995 | Yuan et al. | |
| 5,456,698 A | 10/1995 | Byland et al. | |
| 5,486,174 A | 1/1996 | Fournet-Fayard et al. | |
| 5,486,176 A | 1/1996 | Hildebrand et al. | |
| 5,501,684 A * | 3/1996 | Schlapfer et al. | 606/301 |
| 5,531,747 A | 7/1996 | Ray | |
| 5,536,268 A | 7/1996 | Griss | |
| 5,545,163 A | 8/1996 | Miller et al. | |
| 5,545,167 A | 8/1996 | Lin | |
| 5,582,612 A | 12/1996 | Lin | |
| 5,584,833 A | 12/1996 | Fournet-Fayard et al. | |
| 5,584,834 A | 12/1996 | Errico et al. | |
| 5,591,166 A | 1/1997 | Bernhardt et al. | |
| 5,601,552 A | 2/1997 | Cotrel | |
| 5,603,714 A | 2/1997 | Kaneda et al. | |
| 5,609,592 A | 3/1997 | Brumfield et al. | |
| 5,613,968 A | 3/1997 | Lin | |
| 5,620,443 A | 4/1997 | Gertzbein et al. | |
| 5,628,740 A | 5/1997 | Mullane | |
| 5,651,789 A | 7/1997 | Cotrel | |
| 5,725,528 A | 3/1998 | Errico et al. | |
| 5,733,286 A | 3/1998 | Ralph et al. | |
| 5,735,851 A | 4/1998 | Errico et al. | |
| 5,743,907 A | 4/1998 | Asher et al. | |
| 5,743,911 A | 4/1998 | Cotrel | |
| 5,797,911 A | 8/1998 | Sherman et al. | |
| 5,800,435 A | 9/1998 | Errico et al. | |
| 5,876,403 A | 3/1999 | Shitoto | |
| 5,899,903 A | 5/1999 | Cotrel | |
| 5,938,663 A | 8/1999 | Petreto | |
| 5,947,965 A | 9/1999 | Bryan | |
| 5,947,966 A | 9/1999 | Drewry et al. | |
| 5,951,557 A | 9/1999 | Luter | |
| 5,989,250 A | 11/1999 | Wagner et al. | |
| 5,989,254 A | 11/1999 | Katz | |
| 6,030,389 A | 2/2000 | Wagner et al. | |
| 6,045,552 A | 4/2000 | Zucherman et al. | |
| 6,053,921 A | 4/2000 | Wagner et al. | |
| 6,063,090 A * | 5/2000 | Schlapfer | 606/270 |
| 6,066,140 A | 5/2000 | Gertzbein et al. | |
| 6,074,393 A | 6/2000 | Sitoto | |
| 6,083,224 A | 7/2000 | Gertzbein et al. | |
| 6,117,135 A | 9/2000 | Schlapfer | |
| 6,123,706 A | 9/2000 | Lange | |
| 6,132,430 A | 10/2000 | Wagner | |
| 6,136,000 A | 10/2000 | Louis et al. | |
| 6,136,002 A | 10/2000 | Shih et al. | |
| 6,187,005 B1 * | 2/2001 | Brace et al. | 606/264 |
| 6,206,879 B1 | 3/2001 | Marnay et al. | |
| RE37,161 E | 5/2001 | Michelson et al. | |
| 6,235,034 B1 | 5/2001 | Bray | |
| 6,248,104 B1 | 6/2001 | Chopin et al. | |
| 6,248,105 B1 | 6/2001 | Schlapfer et al. | |
| 6,254,603 B1 | 7/2001 | Gertzbein et al. | |
| 6,261,288 B1 | 7/2001 | Jackson | |
| 6,277,119 B1 | 8/2001 | Walulik et al. | |
| 6,280,445 B1 | 8/2001 | Morrison et al. | |
| 6,287,309 B1 | 9/2001 | Baccelli et al. | |
| 6,306,136 B1 | 10/2001 | Baccelli | |
| 6,344,057 B1 | 2/2002 | Rabbe et al. | |
| 6,355,038 B1 | 3/2002 | Pisharodi | |
| 6,391,030 B1 | 5/2002 | Wagner et al. | |
| 6,413,259 B1 | 7/2002 | Lyons et al. | |
| 6,416,515 B1 | 7/2002 | Wagner | |
| 6,454,769 B2 | 9/2002 | Wagner et al. | |
| 6,458,132 B2 | 10/2002 | Choi | |
| 6,471,704 B2 | 10/2002 | Gertzbein et al. | |
| 6,475,218 B2 | 11/2002 | Gournay et al. | |
| 6,488,682 B2 | 12/2002 | Kikuchi et al. | |
| 6,506,216 B1 | 1/2003 | McCue et al. | |
| 6,547,790 B2 | 4/2003 | Harkey, III et al. | |
| 6,554,831 B1 | 4/2003 | Rivard et al. | |
| 6,562,040 B1 | 5/2003 | Wagner | |
| 6,565,565 B1 | 5/2003 | Yuan et al. | |
| 6,565,605 B2 | 5/2003 | Goble et al. | |
| 6,579,319 B2 | 6/2003 | Goble et al. | |
| 6,585,738 B1 | 7/2003 | Mangione et al. | |
| 6,595,992 B1 | 7/2003 | Wagner et al. | |
| 6,602,254 B2 | 8/2003 | Gertzbein et al. | |
| 6,610,063 B2 | 8/2003 | Kumar et al. | |
| 6,613,050 B1 | 9/2003 | Wagner et al. | |
| 6,613,053 B1 | 9/2003 | Collins et al. | |
| 6,616,664 B2 | 9/2003 | Walulik et al. | |
| 6,620,164 B2 | 9/2003 | Ueyama et al. | |
| 6,641,583 B2 | 11/2003 | Shluzas et al. | |
| 6,641,585 B2 | 11/2003 | Sato et al. | |
| 6,641,586 B2 | 11/2003 | Varieur | |
| 6,663,631 B2 | 12/2003 | Kuntz | |
| 6,669,697 B1 | 12/2003 | Pisharodi | |
| 6,682,530 B2 | 1/2004 | Dixon et al. | |
| 6,682,533 B1 | 1/2004 | Dinsdale et al. | |
| 6,702,814 B2 | 3/2004 | Walulik et al. | |
| 6,702,815 B2 | 3/2004 | Kuntz | |
| 6,726,687 B2 | 4/2004 | Jackson | |
| 6,736,816 B2 | 5/2004 | Ritland | |
| 6,749,613 B1 | 6/2004 | Conchy et al. | |
| 6,755,829 B1 | 6/2004 | Bono et al. | |
| 6,884,241 B2 | 4/2005 | Bertranou et al. | |
| 7,037,340 B2 | 5/2006 | Gau | |
| 2001/0001119 A1 | 5/2001 | Lombardo | |
| 2001/0010000 A1 | 7/2001 | Gertzbein et al. | |
| 2001/0047173 A1 | 11/2001 | Schlaepfer et al. | |
| 2002/0010467 A1 | 1/2002 | Cooper et al. | |
| 2002/0013585 A1 | 1/2002 | Gournay et al. | |
| 2002/0143341 A1 * | 10/2002 | Biedermann et al. | 606/73 |
| 2002/0193795 A1 | 12/2002 | Gertzbein et al. | |
| 2003/0045875 A1 | 3/2003 | Bertranou et al. | |
| 2003/0088251 A1 | 5/2003 | Braun et al. | |
| 2003/0114853 A1 | 6/2003 | Burgess et al. | |
| 2003/0187441 A1 | 10/2003 | Bolger et al. | |
| 2004/0158251 A1 | 8/2004 | Morrison et al. | |
| 2004/0172020 A1 | 9/2004 | Beaurain et al. | |
| 2004/0254577 A1 | 12/2004 | Delecrin et al. | |
| 2005/0010215 A1 | 1/2005 | Delecrin et al. | |
| 2005/0107788 A1 | 5/2005 | Beaurain et al. | |
| 2006/0025769 A1 * | 2/2006 | Dick et al. | 606/61 |

FOREIGN PATENT DOCUMENTS

| | | |
|---|---|---|
| DE | 4201043 A | 7/1993 |
| DE | 19512709 A | 10/1996 |
| DE | 19545612 A | 6/1997 |
| DE | 19605640 A | 8/1997 |
| EP | 0274713 A | 7/1988 |
| EP | 0301489 A | 2/1989 |
| EP | 0490812 A | 6/1992 |
| EP | 0572790 A | 12/1993 |
| EP | 0679369 A | 11/1995 |
| EP | 0846444 | 6/1998 |
| EP | 1254640 A | 11/2002 |
| FR | 2659226 A | 9/1991 |

(56) References Cited

FOREIGN PATENT DOCUMENTS

| | | |
|---|---|---|
| FR | 2683445 | 5/1993 |
| FR | 2697993 | 5/1994 |
| FR | 2702361 A | 9/1994 |
| FR | 2704136 | 10/1994 |
| FR | 2706763 A | 12/1994 |
| FR | 2724108 A | 3/1996 |
| FR | 2726171 A | 5/1996 |
| FR | 2735011 | 12/1996 |
| FR | 2765093 A | 12/1998 |
| FR | 2823095 | 4/2001 |
| FR | 2827150 A | 1/2003 |
| FR | 2831048 | 4/2003 |
| FR | 2831049 | 4/2003 |
| FR | 2833151 | 6/2003 |
| FR | 2859095 | 3/2005 |
| GB | 2178323 A | 2/1987 |
| JP | 09098983 A | 4/1997 |
| WO | WO9307823 | 4/1993 |
| WO | WO9510240 A | 4/1995 |
| WO | WO9900065 | 1/1999 |
| WO | WO9933405 A | 7/1999 |
| WO | WO9956675 A | 11/1999 |
| WO | WO0015125 A | 3/2000 |
| WO | WO0018312 A | 4/2000 |
| WO | WO0101874 A | 1/2001 |
| WO | WO0103592 A | 1/2001 |
| WO | WO0126566 A | 4/2001 |
| WO | WO0228299 A | 4/2002 |
| WO | WO02080788 | 10/2002 |
| WO | WO03032850 A1 | 4/2003 |
| WO | WO03032851 | 4/2003 |
| WO | WO03039400 A2 | 5/2003 |
| WO | WO 03049629 A1 * | 6/2003 ............ A61B 17/70 |
| WO | WO03049629 A1 | 6/2003 |
| WO | WO2005020829 A1 | 3/2005 |

OTHER PUBLICATIONS

FR 2 704 136 Preliminary Search Report, National Institute of Industrial Property (France), Nov. 24, 1993.
FR 2 823 095 Preliminary Search Report, National Institute of Industrial Property (France), Dec. 20, 2001.
FR 2 827 150 Preliminary Search Report, National Institute of Industrial Property (France), Apr. 8, 2002.
FR 2 831 048 Preliminary Search Report, National Institute of Industrial Property (France), Jul. 3, 2002.
FR 2 831 049 Preliminary Search Report, National Institute of Industrial Property (France), Jul. 3, 2002.
FR 2 831 796 Preliminary Search Report, National Institute of Industrial Property (France), Aug. 2, 2002.
FR 2 833 151 Preliminary Search Report, National Institute of Industrial Property (France), Aug. 28, 2002.
FR 2 859 095 Preliminary Search Report, National Institute of Industrial Property (France), Apr. 14, 2004.
PCT/FR98/01363 (Publication WO9900065 Jan. 7, 1999), International Search Report, EPO, Oct. 14, 1998.
PCT/IB02/02827 International Search Report, EPO, Oct. 4, 2002.
PCT/IB02/04306 International Search Report, EPO, Feb. 4, 2003.
PCT/IB02/04307 International Search Report, EPO, Feb. 4, 2003.
PCT/IB02/04642 International Search Report, EPO, Jul. 2, 2003.
PCT/IB02/05302 International Search Report, EPO, Mar. 25, 2003.
PCT/IB04/002825 International Search Report, EPO, Jan. 7, 2005.
PCT/IB02/02827 International Preliminary Examination Report, EPO, May 15, 2003.
PCT/IB02/04306 International Preliminary Examination Report, EPO, Jul. 9, 2003.
PCT/IB02/04307 International Preliminary Examination Report, EPO, Jan. 13, 2004.
PCT/IB02/04642, International Preliminary Examination Report, EPO, Apr. 1, 2004.
PCT/IB02/05302 International Preliminary Examination Report, EPO, Mar. 23, 2004.
PCT/IB04/002825, International Preliminary Report on Patentability, EPO, Oct. 25, 2005.
PCT/IB04/002825, Written Opinion of the International Searching Authority, EPO, Jan. 5, 2005.
Product Bulletin, Acromed Corporation, Date Unknown.
Spinal Instrumentation, An and Cotler, 1992, Williams & Wilkins, pp. 399-400.
Spinal Product Systems, Zimmer, Date Unknown.
Stafix Plate System;Daruma, Date Unknown.
The Syracuse I-Plate, James C. Bayley, Md., et al., Department of Orthopedic Surgery, SUNY-HSC at Syracuse, Spine, vol. 16, No. 3 Supplement, Date Unknown.
TSRH Spinal Implant System, Danek Medical Inc., Date Unknown.
Un nouveau standard: la barre á méplat LDR; Website: www.ldrmedical.fr/easyspine.htm; Sep. 19, 2004.
U.S. Appl. No. 10/276,712, filed Mar. 26, 2003.
U.S. Appl. No. 10/473,999, filed Apr. 12, 2004.
U.S. Appl. No. 10/483,563, filed May 21, 2004.
U.S. Appl. No. 10/476,565, filed Jun. 8, 2004.
U.S. Appl. No. 10/492,827, filed Jul. 15, 2004.
U.S. Appl. No. 10/492,753, filed Aug. 9, 2004.
U.S. Appl. No. 10/498,234, filed Dec. 7, 2004.
U.S. Appl. No. 11/051,710, filed Feb. 4, 2005.
U.S. Appl. No. 11/098,266, filed Apr. 4, 2005.
U.S. Appl. No. 11/109,276, filed Apr. 18, 2005.
U.S. Appl. No. 11/180,868, filed Jul. 13, 2005.
U.S. Appl. No. 10/533,846, filed Nov. 11, 2005.
U.S. Appl. No. 11/341,007, filed Jan. 27, 2006.
U.S. Appl. No. 11/362,253, filed Feb. 24, 2006.
U.S. Appl. No. 10/570,080, filed Feb. 28, 2006.
U.S. Appl. No. 11/378,165, filed Mar. 17, 2006.
U.S. Appl. No. 11/390,711, filed Mar. 27, 2006.
U.S. Appl. No. 10/575,065, filed Apr. 7, 2006; and.
U.S. Appl. No. 10/494,418, filed Jul. 22, 2004.
FR 2 833 151 Preliminary Search Report, National Institute of Industrial Property (France), Apr. 28, 2002.
PCT/IB02/05302 International Preliminary Examination Report, EPO, Mar. 23, 2003.
PCT/IB02/02827 International Search Report, EPO, Oct. 4, 2002; and.

* cited by examiner

OSSEOUS ANCHORING IMPLANT WITH A POLYAXIAL HEAD AND METHOD FOR INSTALLING THE IMPLANT

The present invention relates to an implant providing osseous anchorage in a vertebra, for example to anchor an osteosynthesis device. This implant has a polyaxial head allowing to receive, in a plurality of angular positions, a bar linking several implants. The present invention also relates to a method for installing the implant, in particular to perform a reduction of a spondylolisthesis (i.e., a jutting out of a vertebra with respect to the adjacent vertebrae).

It is known, in the prior art, to fix a plurality of implants, each to a vertebra, and to connect them together with a bar or a plate, fixed to each implant, along the vertebral column, so as to maintain or correct the rachis. These implants are generally fixed to the vertebrae, either via screwing of a threaded part of the implant in a vertebra, or by fixing of a hook of the implant onto a vertebra. The implants known to the prior art are equipped with a fixation channel, at the head, allowing to fix the bar or plate into a duct. Sometimes, a lateral aperture allows introducing the bar via the side of the duct.

The international patent application WO 03/049629 shows an implant with polyaxial head allowing to orient the bar in different positions before fixing it, these positions being restricted by a determined clearance of the bar around the axis of the implant and/or around the axis of the duct, thanks to a ball and socket connection. This polyaxial system allows to simplify the positioning of the bar and to reduce the constraints exercised by the implant on the bar, but offers a limited number of levels of movement (i.e., a limited freedom of motion of the various elements of the implant with respect to each other).

On the other hand, the implants known in the prior art generally allow to completely reduce a spondylolisthesis of the rachis but do not allow to partially reduce it, a spondylolisthesis reduction consisting in a repositioning of the vertebra in the axis of the adjacent vertebrae in the vertebral column. Yet, in some cases, it is necessary to only partially reduce a spondylolisthesis or to control, during implantation, the reduction level of the spondylolisthesis.

The international patent application WO 00/15125 mentions that an implant with polyaxial head allowing to orient the bar in different positions before fixing it. However, the different embodiments of this implant in the prior art have the inconveniences, when the bar is inserted into its duct, of either not offering all the possible levels of movement, or of not allowing to continue to screw the implant into the vertebrae.

The object of the present invention is to overcome these inconveniences in the prior art by proposing an implant for osseous anchoring allowing to restrict the constraints exercised on the rachis during a correcting of the latter and to control the reduction level of a spondylolisthesis.

This object is reached through an implant of osseous anchoring comprising a body equipped with osseous anchoring means and a head bearing fixation means capable of receiving and fixing at least one bar, in particular of osteosynthesis, the head of the implant being traversed by at least one duct receiving the bar through a lateral aperture and by a threaded channel having an axis not parallel to the axis of the duct and receiving a fixation screw of the bar, the implant being characterized in that it comprises fixation means of the head on a part of the body of the implant extending along the osseous anchoring means, these fixation means of the head consisting in a portion of the head which forms a ring into which is inserted a fixation olive threaded onto the part of the body of the implant extending along the osseous anchoring means and allowing, prior to blocking and fixing, at least a determined clearance of the head around at least one axis not parallel to the axis of symmetry of the osseous anchoring means, and in that the fixation screw of the bar comprises a ball and socket at its base allowing at least a determined clearance of the bar around at least one axis parallel to the duct axis, the fixation means of the head and the ball and socket of the fixation screw of the bar allowing a determined clearance of the head around the axis of symmetry of the osseous anchoring means, even when the bar is inserted into the duct.

According to another feature, the inside diameter of the ends of the duct of the head is greater than the inside diameter of the center of the duct, which confers a widened out profile to the duct allowing, in association with the ball and socket at the base of the fixation screw, a determined clearance of the bar around the axis of the duct.

According to another feature, the head is equipped with a ring, which is placed on the other side of the head in relation to the duct, and in that the part of the implant extending along the osseous anchoring means, which is threaded through a fixation olive, itself threaded through a ring, is cylindrical and threaded and extends, widening out from the cylindrical part towards the anchoring means, by a tapered part, complementary of a tapered internal surface of the fixation olive which is sectioned at a point along its entire height.

According to another feature, the external surface of the fixation olive is convex and complementary of a concave internal surface of the ring, the external diameter of the olive being slightly less than the internal diameter of the ring, so that the olive, compression inserted into the ring thanks to the section of the olive along its entire height, allows a retaining of the head on the olive, whilst allowing the orientation and the determined clearance of the head around at least one axis parallel to the axis of symmetry of the osseous anchoring means.

According to another feature, a nut has, along its entire height, a threaded drilling intended to be screwed to the cylindrical part of the implant which is threaded so as to initially provoke, either the rise of the body of the implant up to the bar, or the descending of the olive and the head onto the body of the implant, according to the relative positions of the head, the olive and the body in relation to the bar, then secondly, the leaning of the olive on the tapered part of the implant, which engenders the expansion of the fixation olive, and thus the blocking of the head in the desired position.

According to another feature, the nut is equipped with flats capable of co-operating with a tool adapted to the screwing of the nut to the threaded cylindrical part of the implant.

According to another feature, the osseous anchoring means are a hook.

According to another feature, the osseous anchoring means are a threaded part.

According to another feature, the cylindrical part of the body of the implant is equipped, at its end opposite the osseous anchoring means, with a blind hole with six faces capable of co-operating with a tool adapted to the screwing of the implant.

According to another feature, the ball and socket of the fixation screw of the bar comprises a flat at its base.

According to another feature, the flat at the base of the ball and socket of the fixation screw of the bar consists in a disc prominent at the periphery of the ball and can be used as a stop limiting the movement of the ball in relation to the fixation screw of the bar.

According to another feature, the ball and socket at the base of the fixation screw of the bar is associated with a mobile base located between the bar and the duct in a housing in the duct, this base facilitating, prior to blocking and fixing of the bar, the determined clearance of the bar around at least one axis parallel to the axis of the duct.

According to another feature, the mobile base has formal irregularities co-operating with formal irregularities of the duct, so as to restrict the movement of the base in its housing and therefore restrict the clearance of the bar around the axis parallel to the axis of the duct.

Another object of the invention is to propose a method for installing the implant according to the invention.

This object is reached via a method for preparing out with the body prior to the implanting of an osseous anchoring implant comprising a threaded part extended by a smooth tapered part itself extended by a threaded cylindrical part, said cylindrical part being threaded through a fixation olive itself threaded in a head equipped with a duct receiving an osteosynthesis bar by a lateral aperture and with a channel receiving a fixation screw provided with a ball and socket at its base, the fixation olive and the head being retained by a nut screwed to the cylindrical part, the ball and socket being provided, at its base, with a flat consisting in a disc which is prominent at the periphery of the base of the ball and can thus be used as a stop limiting the rotation of the ball in relation to the fixation screw, the method being characterized in that it comprises at least the following successive steps:

the insertion of the bar, via the lateral aperture, into the duct in which it is at least retained via a partial screwing of a fixation screw;

the positioning of the flat at the base of the ball as a stop in the duct, on its internal surface opposite to the lateral aperture, in order to prevent a rotation of the bar in the duct, thanks to the contact of this flat of the ball with a flat on the bar and, consequently prevent, the descending of the head in relation to the bar;

the partial screwing of the nut on the cylindrical part of the implant, so that the nut comes into contact with the fixation olive, so as to prevent a disengagement of the fixation olive and the head from the cylindrical part of the implant, whilst allowing the movement of the head of the implant around at least the axis of symmetry of the osseous anchoring means, in the expectation of the screwing of the osseous anchoring means which will provoke the rise of the body and the vertebra, followed by the screwing of the nut, which will end the rise of the body and the vertebra and will then block the head and the body in the desired position.

According to another feature, the method comprises at least the following successive steps:

the insertion of the bar, via the lateral aperture, into the duct in which it is at least retained via a partial screwing of a fixation screw;

the positioning of the flat at the base of the ball as a stop in the duct, on its internal surface opposite to the lateral aperture, in order to prevent a rotation of the bar in the duct, thanks to the contact of this flat of the ball with a flat on the bar and, consequently prevent, the descending of the head in relation to the bar;

the partial screwing of the nut on the cylindrical part of the implant, so that the nut comes into contact with the fixation olive, so as to retain the vertical position of the cylindrical part of the implant, in relation to the head, whilst allowing the movement of the head of the implant around at least the axis of symmetry of the osseous anchoring means, in the expectation of the complete screwing of the nut which will provoke the rise of the body and the vertebra and will then block the head and the body in the desired position.

According to another feature, the steps of the partial screwing of the fixation screw and the positioning of the flat at the base of the ball as a stop in the duct, on its internal surface opposite to the lateral aperture, can be replaced by a step of a complete screwing of the fixation screw, so as to prevent any movement of the ball and the bar and, consequently, prevent the descending of the head in relation to the bar.

Other features and advantages of the present invention will be clearer upon reading the description thereafter with reference to the annexed drawings, wherein.

Figure 1:
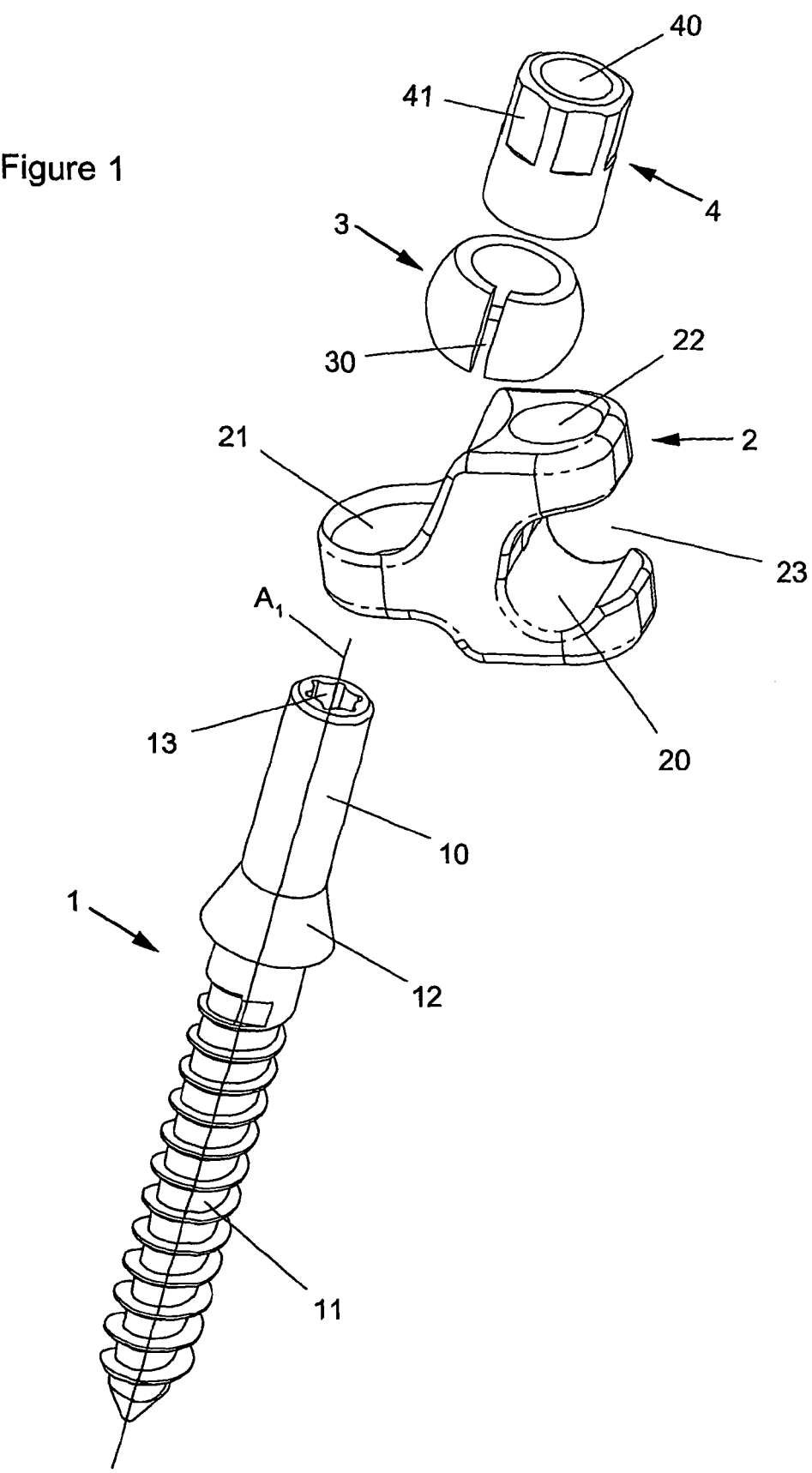
FIG. 1 represents a blown-up perspective view of the osseous anchoring implant according to a first embodiment of the invention.

The osseous anchoring implant according to the invention comprises four elements: a body (1), a head (2), a fixation olive (3) and a nut (4). The body (1) of the implant comprises, at its upper end, a cylindrical part (10) and, at its lower end, osseous anchoring means (11) for anchoring in a vertebra. The cylindrical part (10) is threaded on its external wall. The cylindrical part (10) and the anchoring means (11) are linked via a smooth tapered part (12), whose transversal section increases between the cylindrical part (10) and the anchoring means (11). The weakest section of the tapered part (12) is substantially equal to the transversal section of the cylindrical part (10). The cylindrical part (10), the tapered part (12) and the anchoring means (11) constituting the body (1) of the implant are placed according to a first axis ($A_1$).

The head (2) of the implant comprises a duct (20) allowing to receive a bar (7), which links several implants together within the context of an osteosynthesis device so as to retain, support or correct the rachis when the implants are screwed in vertebrae. The head (2) of the implant is called polyaxial as it has several levels of free movement, thanks to the fact that it is fixed to the body (1) by a ring (21) clamping a fixation olive (3) constituted of a ring with a tapered and smooth internal wall, complementary of the smooth tapered part (12) of the body (1) of the implant. The external wall of the olive (3) is convex and complementary of the internal surface of the fixation ring (21) of the head (2). This freedom of movement of the head (2), in relation to the body (1) of the implant, consists in a rotation or a combination of several rotations according to three axes substantially perpendicular to one another, particularly visible in FIG. 2 and passing through the geometric center of the olive (3). The polyaxial head (2) thus has a determined clearance around at least one axis not parallel to the axis ($A_1$) of symmetry of the osseous anchoring means (11). This clearance is due to the fact that the head (2) is free in rotation around the axis ($A_1$) of the body (1), in rotation around the axis ($A_2$) of the head (2), substantially perpendicular to the axis ($A_1$) of the body (1) of the implant, and in rotation around the axis ($A_5$), substantially perpendicular to the axes ($A_1$) of the body (1) and ($A_2$) of the head and parallel to the axis ($A_4$) of the duct. This freedom of rotation of the head (2) around these axes ($A_1$, $A_2$ and $A_5$) allows a determined clearance of the head (2), in whatsoever direction, around osseous anchoring means notably constituted of the body (1) of the implant. This clearance allows the head (2), in the absence of the fixation bar (7), to follow a circular ring centered on the olive (3) and bearing a shape substantially identical to the external surface of the olive (3) and therefore take whatsoever position in this ring, in relation to the olive (3). The head (2) is equipped with a lateral aperture (23) allowing to introduce the bar via the side of the duct (20). The head (2) also comprises a channel (22) of axis ($A_3$), not parallel (for example substantially perpendicular) to the axis of the duct (20). This channel (22) is threaded so as to receive a fixation screw (5) of the bar (7). The head (2) is also equipped, on the other side of the latter in relation to the duct (20), of a ring (21) whose internal surface is concave, smooth and complementary of the convex and smooth external wall of the fixation olive (3). In relation to the bar (7), the internal surface of the duct (20) is sufficiently large to allow some clearance of the bar (7) in the duct (20).

Figure 5A:
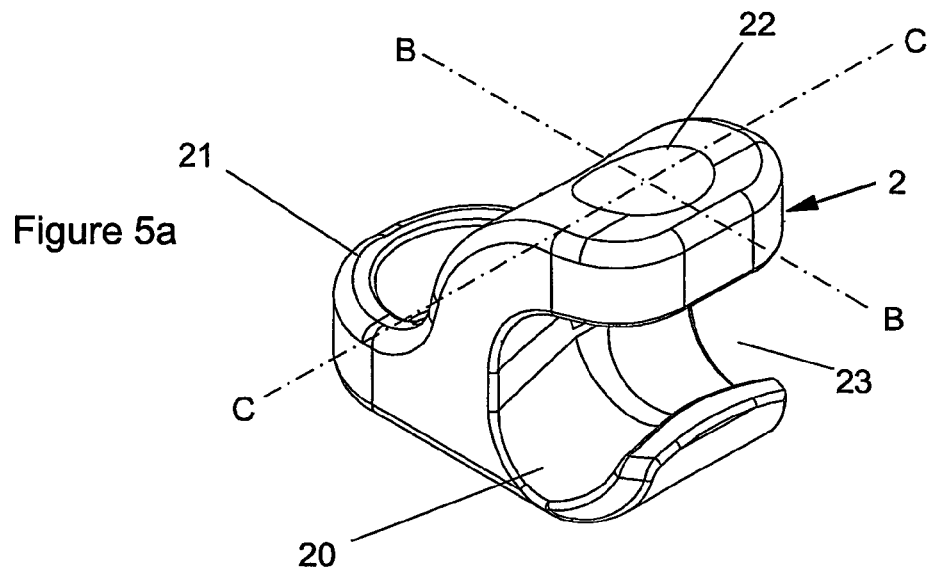
FIG. 5a represents a perspective view of an embodiment of the head of the osseous anchoring implant with the section planes B-B and C-C of FIGS. 5a and 5b, respectively, FIG. 5c also representing the fixation bar and the fixation screw equipped with a ball and socket connection at its base.
Figure 5B:
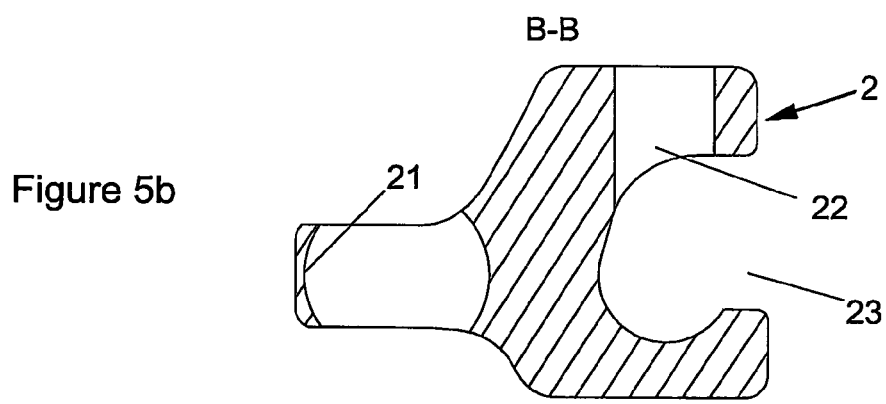
Figure 5C:
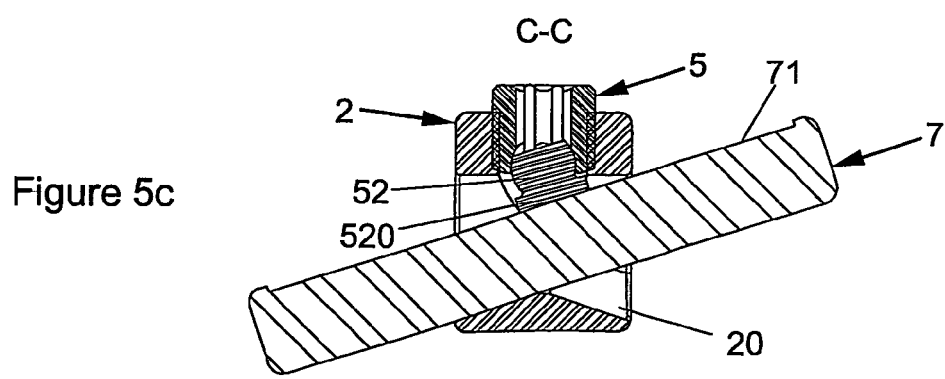
Figure 6A:
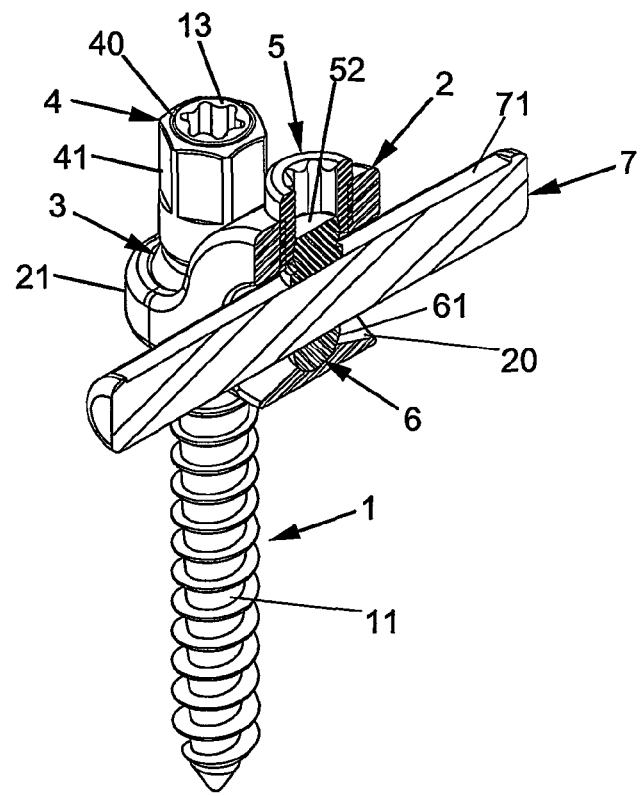
FIGS. 6a and 6b represent sectional views, respectively, according to the axis of the duct and according to an axis perpendicular to the axis of the duct, of the head of the osseous anchoring implant equipped with the fixation bar and the fixation screw equipped with a ball and socket connection at its base and associated with a mobile base.
Figure 6B:
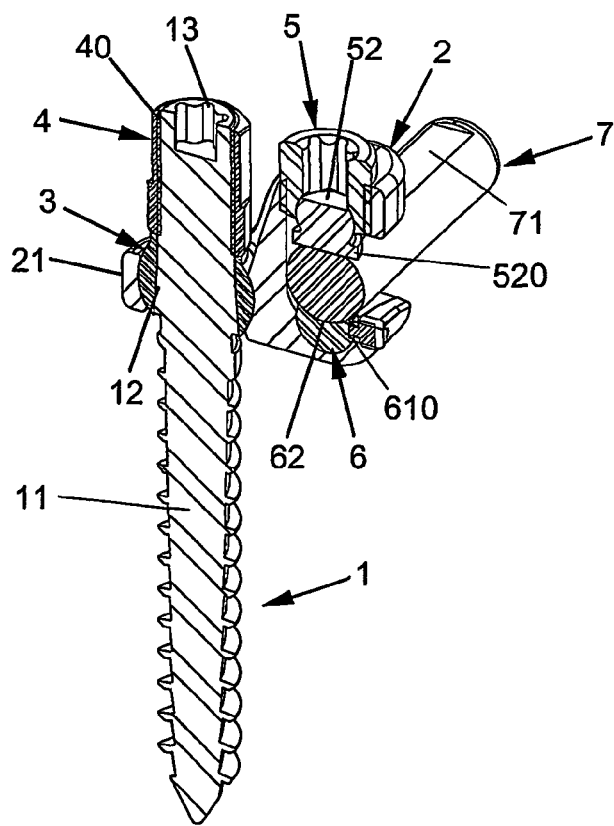

According to an embodiment of the invention, the fixation screw (5) of the bar bears, at its end located on the side of the bar (7), a mobile and articulated element, called ball and socket (52), as that described in the international patent application WO 03/049629 filed by the applicant. The ball and socket (52) consists in a sphere portion (the ball) inserted into a housing (the socket) in the lower end of the fixation screw (5) whose shape is complementary of the sphere portion of the ball and socket (52). This complementary nature of the shape ensures a ball and socket connection between the fixation screw (5) and the bar (7). The ball (52) can have a flat (520) at its base. The bar (7) can also have a flat (71), complementary of the flat (520) at the base of the ball (52), so as to allow a better fixing of the bar (7) when screwing the fixation screw (5) of the bar. This mobile link authorizes some clearance of the ball (52) in relation to the fixation screw (5), in rotation around the center of this ball and socket (52). This ball and socket connection also allows the flat (71) of the bar (7) to remain in contact with the flat (520) of the ball and socket (52) without slippage, which avoids deteriorating the surfaces in contact, renders the blocking more reliable, and reduces the risks of residual stress. In addition, the flat (520) of the ball (52) can consist, as represented on FIGS. 5b, 6a and 6b, in a disc (520) prominent at the periphery of the base of the ball (52). The fact that this disc (520) is prominent at the periphery of the base of the ball (52) and thus protruding in the duct (20) makes it possible to use it as a stop limiting the rotation of the ball (52) in its socket (thus limiting the rotation of the ball in relation to the fixation screw). For instance, the disc (520) can be placed as a stop in the internal surface of the duct (20), on the side opposite to the one where the lateral aperture (23) is. This placement of the disc (520) as a stop prevents the rotation of the bar (7) around the axis ($A_4$) of the duct (20), thanks to the contact between the disc (520) of the flat at the base of the ball (52) and the flat (71) of the bar (7). The corresponding rotation of the head (2) around the axis ($A_5$) is thus also prevented and it prevents the descending of the head (2) in relation to the bar (7). The ball and socket connection (52) can be associated with a widening of the duct (20) whose ends have a diameter greater than that at the center of the duct (20), as particularly visible in FIG. 5c. The bar (7) is thus fixed between the ball and socket (52) and the central part of the duct (20), but has a freedom of movement around its longitudinal axis ($A_4$). This freedom of movement can naturally consist in a rotation of the bar (7) around the axis ($A_3$) of the duct (22) and/or a rotation of the bar (7) around the axis ($A_4$) of the duct (20) and/or a rotation of the bar (7) around an axis parallel to the axis ($A_2$) and passing through the point of intersection between the axes ($A_3$) and ($A_4$). The ball and socket connection (52) at the base of the fixation screw (5) therefore allows a determined clearance of the bar (7) around at least one axis ($A_4$) parallel to the axis of the duct. This clearance allows the bar to follow a conical course with, for its summit, the point of intersection between the axes ($A_3$) and ($A_4$) (that meaning, for example, the center of the duct) and bearing an acute angle at its summit.

In an alternative of the embodiment, the ball and socket (52) can be associated with a mobile base (6) placed between the bar (7) and the duct (20). The base (6) is mobile compared to the fixation head (2) and has on its upper face, called support face (62), in contact with the bar (7), a shape complementary of the external surface of this bar (7), for example in the form of a cylinder portion, which provides a good contact surface when tightening the fixation screw (5) of the bar. This mobile base (6) has a part (61) in the shape of a sphere portion, leaning via a complementary contact in a housing formed in the wall of the duct (20). By virtue of this spherical contact, the mobile base (6) has some freedom of rotation around the center of its spherical part (61). On its part (61) in form of a sphere portion the mobile base (6) can have one or a plurality of irregularities (610) in its shape co-operating with one or a plurality of irregularities in the shape of its housing in the duct (20) of the fixation head (2), so as to form a stop limiting the clearance in rotation of the mobile base. These irregularities (610) can be, for example, a pin protruding from the mobile base and co-operating with a larger dimensioned cavity formed on the complementary contact surface. On the contrary, the pin can be in the head (2), at the housing in the duct (20), and protruding into this housing so as to co-operate with a larger dimensioned cavity in the base (6), as for example the pin formed by the screw shown in FIG. 6b, fixed in the head (2), at the housing in the duct (20). This stop, for example, allows avoiding excessive turning of the mobile base (6) and assuring that it properly presents its support facing the bar (7). Just as when the ball and socket (52) is associated with a widening of the duct (20), the bar (7), clamped between the ball and socket (52) and the mobile base (6), has a freedom of movement around its longitudinal axis ($A_4$), in any direction, for example by a combination of rotations around the axes described for the above alternative of the embodiment. The embodiment alternative including the mobile base (6) additionally allows that this freedom of movement is restricted thanks to the irregularities (610) co-operating with the irregularity (or irregularities) of the housing in the duct (20) of the head (2).

Thus, it can be understood that the bar (7) can be inserted and blocked in different angular positions inside the duct (20), while providing a flat contact surface both with the fixation screw, possibly including the ball and socket (52) and with a part of the wall of the widened out duct (20) or with the support face (62) of the mobile base (6). It can also be understood that the invention has the advantage of providing different elements of the implant with a complete freedom of movement in relation to one another. Indeed, the head (2) has, as previously indicated, a freedom of movement around the center of the olive (3) and the bar (7) has a freedom of movement around, for example, the center of the duct (20), thanks to angular clearances by rotation around the axes represented in FIG. 2. Thus, all the possible levels of freedom are reached for the position of the head (2) in relation to the body (1) of the implant and for the bar (7) in relation to the duct (20) of the head (2). The combination of these levels of freedom of the head and of the bar provide the implant of the present invention with the advantage of allowing a clearance, in every direction, of the bar (7) in relation to the body (1) of the implant. In particular, even when the bar (7) is inserted into the duct (20) of the head (2), the position of the bar (7) can be adjusted, for example, thanks to a rotation of the head around the axis (A.sub.1) of the body of the implant and a rotation of the bar substantially around the axis (A.sub.3) of the channel (22) of the fixation screw. These possible rotations are particularly interesting for the reduction of a spondylolisthesis, because the natural movement of a vertebra during this reduction is substantially circular. It is thus of particular interest to provide the implant with a freedom of movement during the reduction. Only an implant as the present invention, combining a polyaxial head (2) with a ball and socket (52), allows this freedom of movement facilitating the reduction of the spondylolisthesis. Even when the bar (7) is inserted into the duct (20), the invention allows for a determined clearance of the head (2) around the axis of symmetry (A.sub.1) of the osseous anchoring means. This clearance allows the head (2) to follow a conical course, if the bar (7) inserted into the duct (20) is not fixed, a cone whose base has a perimeter in the shape of a disc or ellipse, whose summit is located at the center of the olive (3) and which has an acute angle at its summit. The different angular clearances allow to insert the bar (7) into the head (2) with greater ease and to obtain a tightening of the bar in its most natural position in relation to the implants, which reduces or cancels out the stresses that could remain in the device after tightening. Moreover, the tightening efforts converge in this way directly to the blocking without having to conflict with the rigidity of the bar, and the reliability of the blocking is therefore improved. The bar is fixed to the head (2) via screwing of the fixation screw (5) in the channel (22) once the bar is in the desired position. The fixation olive (3) is constituted of a ring with a tapered and smooth internal wall, complementary of the smooth tapered part (12) of the body (1) of the implant. The external wall of the olive (3) is convex and complementary of the internal surface of the fixation ring (21) of the head (2). The olive (3) is sectioned at a point (30) of the ring, along the entire height of the latter. The minimum diameter of the tapered internal wall of the ring is slightly greater than the external diameter of the cylindrical part (10) of the body of the implant, so that the cylindrical part (10) of the body (1) of the implant can be threaded into the olive. The olive (3) is inserted into the fixation ring (21) of the head (2) by applying pressure to the olive (3) which compresses thanks to the section made along its height, to allow its insertion into the ring (21), then by releasing the pressure on the olive (3) so as to allow it to dilate in the ring (21). The positioning and the retaining of the olive (3) in the ring (21) is thus done automatically thanks to the complementary nature between its convex external wall of the olive (3) and the concave internal surface of the ring (21) and thanks to the fact that the olive has an external diameter slightly smaller than the internal diameter of the ring.

The nut (4) comprises at its center, and along its height, a threaded cylindrical drilling (40), of internal diameter substantially equal to the external diameter of the cylindrical part (10) of the body (1) of the implant. The nut (4) comprises on its external wall a plurality of flats (41) allowing to screw the nut (4) to the cylindrical part (10) of the body of the implant using an adapted tool, for example a monkey wrench.

Figure 2:
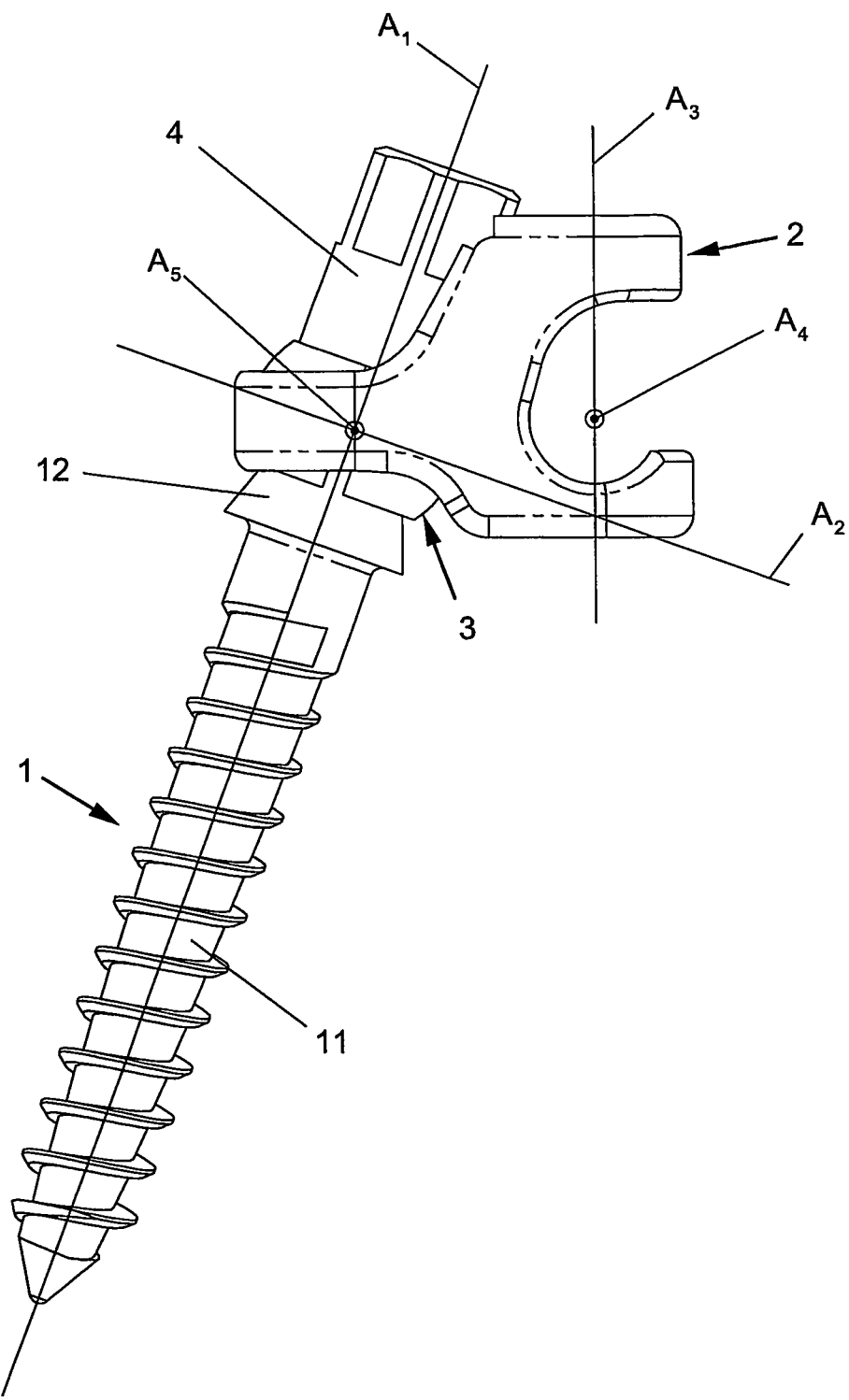
FIG. 2 represents a side view of the osseous anchoring implant according to the embodiment of FIG. 1.

In a first embodiment represented in FIGS. 1 and 2, the anchoring means (11) of the body (1) of the implant are an extended part comprising a thread, which is intended to be screwed into the osseous matter, for example at the pedicle or the body of a vertebra, or in the sacrum. To facilitate the installing of the body (1) of the implant, the upper part of the cylindrical part (10) of the body (1) of the implant is fitted with a blind hole (13) with six faces, which is of a complementary nature of a known screwing tool of the implant. It is to be noted that thanks to the drilling (40) performed along the entire height of the nut (4), this blind hole (13) remains accessible for screwing of the osseous anchoring means (11), even when the nut (4) is inserted on the cylindrical part (10) of the body (1) of the implant.

Figure 3:
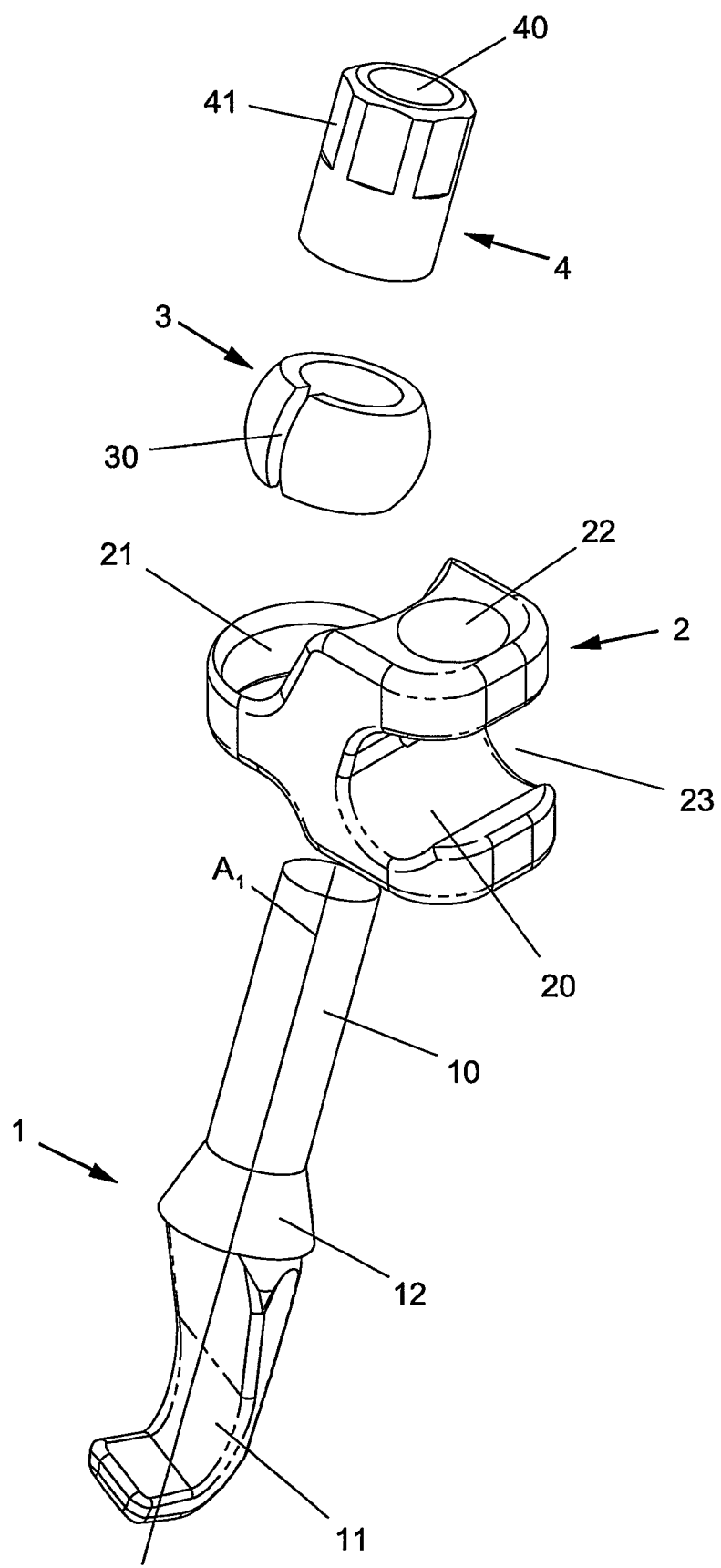
FIG. 3 represents a blown-up perspective view of the osseous anchoring implant according to another embodiment of the invention.
Figure 4:
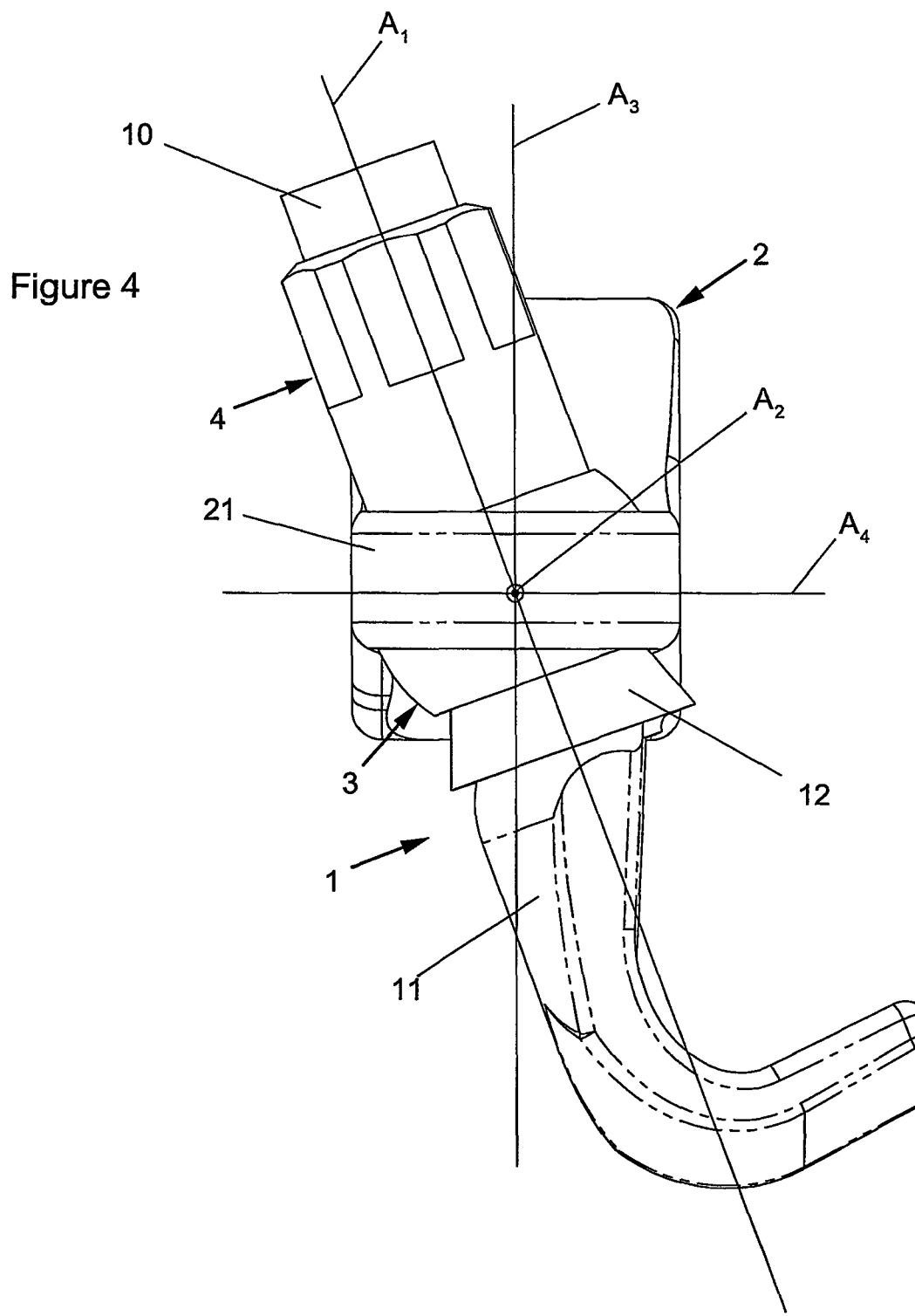
FIG. 4 represents a side view of the osseous anchoring implant according to the embodiment of FIG. 3.

In a second embodiment represented in FIGS. 3 and 4, the anchoring means (11) of the body (1) of the implant are a hook, intended to be hooked onto a formal irregularity of the osseous element, such as a pedicle, a blade or a vertebrae transversal apophysis.

As aforementioned, the fixation olive (3) is inserted into the ring (21) of the head (2) and stays automatically retained there thanks to the complementary nature between the shape of the convex external surface of the olive (3) and the concave internal surface of the ring (21). The fixation olive (3) and the head (2) are threaded to the cylindrical part (10) of the body (1) of the implant, as far as the tapered part (12) of the body, complementary of the tapered internal surface of the olive (3). The nut (4) is partially screwed onto the cylindrical part (10) of the body (1) of the implant, so as to retain the head (2) and the fixation olive (3) on the cylindrical part (10) of the body (1) of the implant, whilst maintaining their freedom of movement. Thus, the head (2) can be orientated in any given direction, thanks to its rotation around the aforementioned axes ($A_1$, $A_2$ et $A_5$). At this stage, the different elements of the implant do not need to be integrally retained between themselves as the olive (3) automatically holds in the ring (21) and on the tapered part (12) of the body (1). The head (2) will therefore be spontaneously vertically stable compared to the body (1) of the implant, only its orientation, according to the different possible angular clearances, requires a screwing of the nut (4) in order to be stabilized. As aforementioned, the blind hole (13) with six faces, allowing the screwing of the body (1) of the implant, remains accessible even when the nut (4) is threaded onto the threaded part (10) of the body (1), the relative vertical stability of the unit made of the head and the olive on the body of the implant will allow to screw the body (1) of the implant driving the head and the olive. When the bar (7) is fixed, the screwing of the nut (4) on the threaded part (10) of the body (1) of the implant will allow, thanks to this relative stability of the head and the olive in relation to the body, either the rise (the ascension) of the body of the implant if the latter was too low compared to the bar (7), or the lowering of the olive and the head on the body if the first elements were too high compared to the latter and the bar (7). Then the screwing of the nut provokes the contact of the olive on the tapered part (12) of the body engendering the dilating of the olive and the blocking of the head according to the desired orientation.

The implant according to the invention is particularly useful for reducing the jutting out of a vertebra of the rachis compared to a first vertebra.

In a first embodiment of the method for installing the implant such as represented in FIGS. 1 and 2, the body (1) of the implant, fitted with the fixation olive (3) the head (2) and the nut (4), is screwed into the jutting out vertebrae until the duct (20) arrives substantially at the same level as a bar (7) already fixed in another implant previously fixed to the first vertebrae. The bar (7) is then inserted into the duct (20) of the head (2) via the lateral aperture (23) and is retained in the duct (20) via a partial screwing of the fixation screw (5) in the channel (22) of the head (2). The disc (520) of the flat at the base of the ball (52) is placed at the contact of the flat (71) of the bar (7) and as a stop in internal surface of the duct (20) of the head (2), on the opposite side lateral aperture (23), so as to prevent the lowering (i.e., descending) of the head (2) in relation to the bar (7). Another possibility for preventing the descending of the head (2), via a rotation of the bar (7) around the axis (A.sub.4) and an associated rotation of the head (2) around the axis (A.sub.5), consists in a complete screwing of the fixation screw (5) which will then prevent any possible rotation of the ball (52) in its socket. Nevertheless, as aforementioned, the natural movement of a vertebra during the reduction of a spondylolisthesis necessitate a freedom of movement of the implant, particularly a freedom of rotation of the head (2) around the axis (A.sub.1) of the body (1) and a freedom of rotation of the bar (7) around the axis (A.sub.3) of the channel (22). It is thus better to prevent the lowering of the head (2) by placing the ball (52) as a stop in the duct (20), so as to allow the rotations of the head (2) and the bar (7) around their two other possible axis. The method continues with the partial screwing of the nut (4) on the cylindrical part (10) of the body (1) of the implant, so that it comes into contact with the fixation olive (3). In this manner, the vertical position of the head (2) is retained in relation to the body (1) of the implant whilst allowing the movement of the head (2) in relation to the body (1) of the implant, around the axes (A.sub.1), (A.sub.2) and (A.sub.5). The head (2) and the fixation olive (3) can not be disengaged from the cylindrical part (10) of the body (1), even if a downward force is applied to the body (1). The method continues with the screwing of the body (1) of the implant in the jutting out vertebra, thanks to the blind hole (13) with six faces. The head (2) of the implant being substantially motionless in the vertical position compared to the bar (7), thanks to the disc (520) of the ball placed as a stop, the traction due to the screwing of the osseous anchoring means (11) of the body (1) engenders the correcting of the jutting out vertebra, thanks to the rise of the body (1) along its axis (A.sub.1), whilst the olive (3) and the head (2) stay vertically stable in relation to the bar (7). The vertebra can now be returned to a level chosen by the person implementing the method, which is no more than the same as the first vertebra. The reduction of a spondylolisthesis is generally more difficult at the end of its course than at the beginning. The screwing of the osseous anchoring means (11) coming with a reduction of the jutting out of a vertebra may thus become more and more difficult while the jutting out is reduced. The reduction thus includes a risk of a tearing out of the osseous anchoring means (11) from the vertebra. Thus, at the end of the reduction, it is better to screw the nut (4) than the osseous anchoring means (11), in order to end the rise of the body (1) and the vertebra. Then, when the vertebra has been brought back to an appropriate level, the head (2) is fixed to the body (1) of the implant via complete screwing of the nut (4) on the cylindrical part (10) of the body of the implant, which engenders the pushing of the fixation olive (3) towards the tapered part (12) of the body (1) of the implant. Under this pressure, the fixation olive (3) undergoes an expansion when its tapered and smooth internal wall starts to come into contact with the tapered part (12) of the body (1) of the implant. The head (2), whose ring (21) clasps the fixation olive (3), is then blocked in the desired position, the internal diameter of the ring (21) being slightly greater than that of the fixation olive (3). If it has not already been, the bar is then fixed to the head (2) of the implant via complete screwing of the fixation screw (5) in the channel (22) of the head (2).

In a second embodiment of the method for installing the implant such as represented in FIGS. 1 and 2, the body (1) of the implant fitted with the fixation olive (3), the head (2) and the nut (4), is screwed into the jutting out vertebrae until the duct (20) arrives substantially at the same level as a bar (7) already fixed in another implant previously fixed to the first vertebrae. The bar (7) is then inserted into the duct (20) of the head (2) via the lateral aperture (23) and is at least retained via screwing of the fixation screw (5) in the channel (22) of the head (2). As aforementioned, the disc (520) of the flat at the base of the ball (52) can be placed at the contact of the flat (71) of the bar (7) and as a stop in internal surface of the duct (20) of the head (2), on the opposite side lateral aperture (23), so as to prevent the lowering (i.e., the descending) of the head (2) in relation to the bar (7). This lowering can also be prevented by a complete screwing of the fixation screw (5), so as to block the ball and socket (52) and thus prevent the rotation of the bar (7) in the duct, because of the contact between the flat (71) of the bar (7) and the flat (520) of the ball (52). We then continue to screw the body (1) of the implant into the jutting out vertebrae to lower it by a distance chosen by the person implementing the method, and which corresponds to no more than the gap of the jutting out vertebrae compared to the first vertebrae. The nut (4) is then completely screwed down, which results in rising the implant, and therefore the jutting out vertebrae, by the distance travelled by the implant once the bar (7) was introduced in the duct (20) of the head, therefore moving it said distance. This embodiment of the method can be chosen when the initial jutting out of the vertebra is not very big and the length of the cylindrical and threaded part (10) of the body is sufficient for reducing the spondylolisthesis. This embodiment has the advantage to limit the risks of tearing out the osseous anchoring means (11) from the vertebra since their screwing in the osseous matter is performed in the absence of the constraints due to the vertical stability of the head (2). As long as the nut (4) is simply in contact with the fixation olive (3), this correcting of the vertebrae is performed by the fraction produced by the bar (7) on the head (2) under the effect of the screwing of the nut (4), thanks to the stability of the olive (3) and therefore of the head (2), in relation to the body (1), thanks to the contact between the flat (71) of the bar (7) with the stop formed by the disc (520) of the ball, as aforementioned. The screwing of the nut (4) thus corrects the position of the vertebra and the body 0, via rising of the body (1) along its axis (A.sub.1), whilst the olive (3) and the head (2) stay vertically stable in relation to the bar (7) and then engenders the fixing of the head (2) onto the body (1) of the implant via expansion of the fixation olive (3) which produces the blocking of the head (2) in the desired position. If it has not already been, the bar (7) is then fixed to the head (2) of the implant via complete screwing of the fixation screw (5) in the channel (22) of the head (2).

In a third embodiment of the method for installing the implant such as represented in FIGS. 3 and 4, the body (1) of the implant, fitted with the fixation olive (3), the head (2) and the nut (4), is hooked to a formal irregularity of the jutting out vertebrae, thanks to the hook of the body (1) visible in FIGS. 3 and 4. The bar is then inserted into the duct (20) of the head (2) via the lateral aperture (23) and is at least retained, even fixed, via screwing of the fixation screw (5) in the channel (22). The method continues with the screwing of the nut (4), which results in rising the body (1) of the implant, and thus the jutting out vertebrae, by moving it to a level chosen by the person implementing the method, which is no more than the first vertebrae, and as long as the nut (4) is simply in contact with the fixation olive (3), then engenders the fixing of the head onto the body (1) of the implant via expansion of the fixation olive (3) which produces the blocking of the head (2) in the desired position. If it has not already been, the bar is then fixed to the head (2) of the implant via complete screwing of the fixation screw in the channel (22) of the head (2).

In these three embodiments of the method, the raising of the jutting out vertebrae to a level chosen by the person implementing the method, performed according to a curve, the polyaxiality of the connection between the body (1) of the implant and the head (2), via the possibility of rotation around the axes ($A_1$), ($A_2$) and ($A_5$), is then entirely suitable. If the fixation screw (5) does not comprise a flat at its base but instead a ball and socket (52), possibly associated to a mobile base (6) placed between the bar (7) and the duct (20), the implant is provided with a double polyaxiality allowing to further reduce the stresses on both the rachis and the bar, thanks to the possibilities for rotating the head (2) around the axes ($A_1$), ($A_2$) and ($A_5$), even when the bar (7) is inserted in the duct (20) of the head (2).

It should be clear to the specialist in the art that the present invention enables embodiments in many specific forms without moving it away from the field of application of the invention as claimed. Consequently, the present embodiments must be considered as illustrative, but can be modified in the field defined by the import of the attached claims and the invention should not be limited to the details provided above.

The invention claimed is:

1. Method for installing an osseous anchoring implant comprising a body comprising a threaded osseous anchor with an anchor axis, the body also comprising an extending part with a threaded cylindrical part and a tapered part; a head comprising a duct, a lateral aperture and a threaded channel, the duct being configured to receive an osteosynthesis bar comprising a land and the threaded channel being configured to receive a fixation screw comprising a ball and socket with a flat base; a fixation olive co-operative with the extending part of the body; a nut comprising a threaded bore co-operative with the threaded cylindrical part of the extending part of the body; and a retaining ring of the head configured to receive the fixation olive; the method comprising the following steps:

inserting the osteosynthesis bar through the lateral aperture into the duct;

rotating the fixation screw to dispose the flat base of the ball and socket at the land of the osteosynthesis bar to retain the osteosynthesis bar in the duct;

rotating the nut to contact the fixation olive and retain the head while allowing movement of the head around the anchor axis;

rotating the threaded osseous anchor in a vertebra to raise the vertebra; and rotating the nut to block the head and the body in the desired position.

2. Method for installing an osseous anchoring implant comprising a body comprising a threaded osseous anchor with an anchor axis, the body also comprising an extending part with a threaded cylindrical part and a tapered part; a head comprising a duct, a lateral aperture, and a threaded channel, the duct being configured to receive an osteosynthesis bar comprising a land and the threaded channel being configured to receive a fixation screw comprising a ball and socket with a flat base; a fixation olive co-operative with the extending part of the body; a nut comprising a threaded bore co-operative with the threaded cylindrical part of the extending part of the body; and a retaining ring of the head configured to receive the fixation olive; the method comprising the following steps:

inserting the osteosynthesis bar through the lateral aperture into the duct;

rotating the fixation screw to dispose the flat base of the ball and socket at the land of the osteosynthesis bar to retain the osteosynthesis bar in the duct;

rotating the nut to contact the fixation olive and maintain the position of the head with respect to the body while allowing movement of the head around the anchor axis; and tightening the nut to raise the body and the vertebra and block the head and the body in the desired position.

* * * * *